United States Patent [19]
Hart

[11] Patent Number: 6,071,093
[45] Date of Patent: *Jun. 6, 2000

[54] BEARINGLESS BLOOD PUMP AND ELECTRONIC DRIVE SYSTEM

[75] Inventor: Robert M. Hart, Arlington, Mass.

[73] Assignees: Abiomed, Inc.; Danvers, Inc.

[*] Notice: This patent issued on a continued prosecution application filed under 37 CFR 1.53(d), and is subject to the twenty year patent term provisions of 35 U.S.C. 154(a)(2).

[21] Appl. No.: 08/733,981

[22] Filed: Oct. 18, 1996

[51] Int. Cl.$^7$ .................................................. F04B 17/04
[52] U.S. Cl. ...................... 417/424.2; 417/420; 604/151; 384/100
[58] Field of Search .............................. 417/420, 423.12, 417/423.13, 424.2; 604/151; 384/100

[56] References Cited

U.S. PATENT DOCUMENTS

| | | | |
|---|---|---|---|
| Re. 28,742 | 3/1976 | Rafferty et al. | 415/90 |
| 3,107,310 | 10/1963 | Carriere et al. | 310/103 |
| 3,647,324 | 3/1972 | Rafferty et al. | 417/420 |
| 3,864,055 | 2/1975 | Kletschka et al. | 415/1 |
| 3,957,389 | 5/1976 | Rafferty et al. | 415/1 |
| 3,970,408 | 7/1976 | Rafferty et al. | 415/60 |
| 4,037,984 | 7/1977 | Rafferty et al. | 415/60 |
| 4,135,253 | 1/1979 | Reich et al. | 3/1.7 |
| 4,779,614 | 10/1988 | Moise | 600/16 |
| 4,944,748 | 7/1990 | Bramm et al. | 623/3 |
| 4,984,972 | 1/1991 | Clausen et al. | 417/420 |
| 5,017,103 | 5/1991 | Dahl | 417/420 |

(List continued on next page.)

OTHER PUBLICATIONS

Delamare, J. et al., "A Compact Magnetic Suspension with only one Axis Control," *IEEE Transactions on Magnetics*, vol. 30, No. 6, 4746–4748 (1994).

(List continued on next page.)

*Primary Examiner*—Timothy S. Thorpe
*Assistant Examiner*—Ehud Gartenberg
*Attorney, Agent, or Firm*—Thomas J. Engellenner; David A. Lane, Jr.

[57] ABSTRACT

A magnetically operated blood pump includes a rotor with an impeller that rotates within a housing, and the housing fastens to a driver that preferably electromagnetically controls the speed and disposition of the impeller in response to sensed conditions. The impeller and housing constitute a disposable assembly in which permanent magnets embedded in the impeller stabilize its position to maintain pumping tolerances in at least one dimension, and also couple to external fields to rotate the impeller. In one embodiment concentric arrangements of cylinder magnets passively maintain radial centering, while coils in the driver are actuated to simultaneously produce a rotational torque and to correct axial or tilt displacements. In a preferred embodiment of this type, sensors around the periphery detect axial displacement and/or tilt as the impeller turns, while the drive circuit responds to the sensor signal to produce compensating phase changes in the coil drive signals. The drive coils are disposed in a common plane and are symmetrically spaced about the central axis, and the phase changes in their drive signals result in a compensating axial force, which may be different in each of the coils to correct tilt. In another or further embodiment, the rotor is freely suspended such that blood washes over one or more surfaces of the rotor, and fluid pressure produces a net restoring force on the rotor to counteract changes in tilt or axial position within the housing. In this case, the driver need only drive rotation of the pump. The drive unit works with a variety of multipole impeller pumps, including ones with magnetic segmented rotors and conventional mechanical support bearings such as ones with a jewel or shaft bearing element. In other embodiments, plural sets of magnets provide passive constraint of radial disturbances and two tilt movements, while axial disturbances are corrected either passively by hydrodynamic surfaces or actively with the driver. The driver unit may include a hand crank assembly, enabling continued operation during power outages.

97 Claims, 10 Drawing Sheets

U.S. PATENT DOCUMENTS

| | | |
|---|---|---|
| 5,078,741 | 1/1992 | Bramm et al. ............................... 623/3 |
| 5,208,522 | 5/1993 | Griepentrog et al. ................... 318/611 |
| 5,360,317 | 11/1994 | Clausen et al. ......................... 415/206 |
| 5,385,581 | 1/1995 | Bramm et al. ............................... 623/3 |
| 5,405,251 | 4/1995 | Sipin ....................................... 417/420 |
| 5,458,459 | 10/1995 | Hubbard et al. ......................... 415/206 |
| 5,507,629 | 4/1996 | Jarvik .................................... 417/423.3 |
| 5,547,350 | 8/1996 | Rawal et al. ............................. 417/354 |
| 5,575,630 | 11/1996 | Nakazawa et al. ....................... 417/420 |
| 5,608,278 | 3/1997 | Mey et al. ................................ 310/90 |
| 5,649,814 | 7/1997 | Lund-lack ............................. 417/423.7 |
| 5,683,231 | 11/1997 | Nakazawa et al. ...................... 417/420 |
| 5,686,772 | 11/1997 | Delamare et al. ...................... 310/90.5 |
| 5,691,586 | 11/1997 | Yonnet et al. ......................... 310/75 D |
| 5,713,730 | 2/1998 | Nose et al. .......................... 417/423.12 |
| 5,840,070 | 11/1998 | Wampler ................................. 604/131 |

OTHER PUBLICATIONS

Hart, R. et al., "A Magnetically Suspended Implantable Centrifugal Blood Pump," *3rd Congress of the International Society for Rotary Blood Pumps*, Houston, No. 36 (Aug. 24–27 1995); Abstract Only.

Yonnet, J.P., "Permanent Magnet Bearings and Couplings," *IEEE Transactions on Magnetics*, vol. MAG–17, No. 1, 1169–1173 (1981).

"A Magnetically Suspended Implantable Centrifugal Pump" Robert M. Hart, Victor G. Filipenco, Robert T.V. Kung, 3rd Congress of the International Society for Rotary Blood Pumps, Houston, 6 viewgraphss, Aug. 1995.

"A Magnetically Suspended and Hydrostatically Stabilized Centrifugal Blood Pump", Robert M. Hart, Victor G. Filipenko, and Robert T.V. Kung, Artificial Organs, 20(6):591–596, 9 refs., Jun. 1996.

"Design considerations for Bearingless Rotary Pumps", Robert T.V. Kung and Robert M. Hart, Artificial Organs, 21(7):645–650, 10 refs., Jul. 1997.

Schima, H., et al., "An Implantable Seal–less Centrifugal Pump with Integrated Double–Disk Motor" Artificial Organs, 19(7) 639–643, Jul. 1995.

Yamane, T. et al., "Design of a Centrifugal Blood Pump with Magnetic Suspension," Artificial Organs, 19(7), 625–630, Jul. 1995.

Proceedings of the Third Congress of the International Society for Rotary Blood Pumps, (ISRP), Houston Texas, Aug. 24–27, 1995, published in Artificial Organs, vol. 20, No. 6, Jun. 1996.

Khanwilkar, Pratap et al., "Using Hybrid Magnetic Bearings to Completely Suspend the Impeller of a Ventricular Assist Device," Artificial Organs 20(6):597–604 (1996).

BEARINGLESS BLOOD PUMP AND ELECTRONIC DRIVE SYSTEM

BACKGROUND

The present invention relates to fluid pumps and to specialized pumping assemblies such as blood pumps, left ventricular assist devices (LVADs) and artificial hearts. It particularly relates to magnetically operated rotating pumps—that is, pumps in which rotational motive power is applied to pump the fluid by an arrangement of driven magnets or electromagnets—and to rotary pumps wherein magnets serve to support and align the rotor, or function as bearings. The invention also relates to drive assemblies and control systems for rotary magnetic blood pumps.

A number of reasonably effective blood pumps are currently available in the market place for providing pumping circulation during relatively short periods, e.g., intervals of a few hours or a day, to supplement or replace normal cardiac circulatory function.

One of these pumps, known as the St. Jude pump after its developing institution, has a broad, relatively flat impeller situated within a housing that has inlet and outlet tube connector ports. The impeller has a generally disc-shaped lower body portion with vanes on its upper surface and an inlet at the center, so that blood entering at the inlet along a central rotation axis is urged radially outward by the vanes to exit at higher pressure along an outflow path at the disc periphery. A shaft extending through the bottom of the disc on the opposite side from the vaned top surface centers the assembly, with the rotation shaft and bearings being located out of the blood flow path and shielded therefrom by seals. Multiple circumferentially-spaced ferromagnetic plates are embedded in the disc body portion, and the pump assembly is driven by a separate driver unit that fastens to the housing and rotates a similarly-poled magnetic disc positioned directly below and closely parallel to the impeller so that the driver disc magnetically engages the plates on the rotor. Some construction details of this pump are further shown in U.S. Pat. No. 5,017,103.

Another currently available pump, sold by Bio-Medicus, Inc. of Minnetonka, Minn. has a rotor assembly in a housing wherein the impeller has a built-up disc body, which, rather than vanes, has several successive sheet-like curved upper surfaces that are arranged at different closely spaced heights along the vertical rotation axis, and to which the blood is delivered at the center of each surface from a central inlet. Each surface is smooth and continuous, without vanes, and the surfaces each engage blood by surface friction to carry it around and drive it outwardly, thus creating gentle pumping action which is less traumatic to blood cells; the multiple top surfaces collectively provide a large active pumping surface area. The bottom of this impeller disc is flat, and has one multi-poled magnet or a number of separate magnets embedded therein to provide six magnetic pole regions spaced at equal angular sectors. As in the St. Jude pump, the pump is driven by a drive unit that mounts with a bayonet fitting parallel to the underside of the disc to engage the impeller with a similarly-sized driver having corresponding poles, so that the magnetic coupling between the impeller and the driver causes the impeller to turn at the speed of the driver. Various aspects of this pump are described in U.S. Pat. Nos. 3,647,324; 3,864,055; 3,957,389; 3,970,408; 4,037,984; and Re 28,742.

Each of these constructions has a shaft and bearing structure which, of necessity, involves seals and generates heat that may potentially lead to blood cell injury or flow disturbances. Furthermore, each involves a certain amount of dead space which may lead to regions of flow stagnation that could engender sepsis or thrombic accumulations. Mechanical bearings may also shed lubricant or foreign particulate matter into the blood. Thus, while the permanent magnet construction of the rotor, and the rigid axial suspension with a separate drive advantageously allow the pump itself to be entirely free of internal coils and electrical feed-throughs, the rotor design and suspension retain certain conventional mechanical features which may pose risks when used as a blood pump.

It is possible to design a motor, (generator, or turbine such that the rotor is entirely magnetically suspended, as suggested for example, in U.S. Pat. No. 5,208,522. In such constructions, several different sets of magnets are arranged to provide forces to maintain a desired axial alignment, and forces for maintaining a desired radial centricity. In practice, when a fixed mechanical shaft bearing is absent, a magnetic suspension may require control of five degrees of freedom, since two tilt components must be addressed in addition to the three translational coordinates. Such technology would allow one to implement a blood pump as an essentially free-floating, magnetically suspended impeller body in a flow path. Nonetheless, the net amount of force which can be generated by a magnetic bearing is highly dependent on the magnets employed and the gaps over which they are required to act, and to apply this architecture to a blood pump would further need to address the mechanical forces caused by blood flow, as well as constraints on flow that are peculiar to blood pumping. Any active control further requires both a suitable set of position or force sensors, and an effectively implemented control regimen. These considerations all affect the weight, rotational inertia, coil size, drive current requirements and potential physical geometry or shape of the assembly, and implicate such characteristics as cost, size, energy efficiency, reliability, heat generation, thrombogenicity and the like. For these reasons, it is not immediately clear whether such a motor could be implemented, or whether a blood pump designed along these principles would have, or could have, desirable or improved operating characteristics.

One approach to building a magnetically suspended pump is shown in U.S. Pat. No. 4,944,748 and a number of later continuation patents derived therefrom. As set forth in those patents, coils in the housing of a pump body may respond to rotor position measurements derived from an LED/photodetector sensing arrangement, and from a sensed pump pressure, to determine an appropriate level of axial force to be applied to the pump rotor and then produce corresponding corrections in the power provided to magnets of the unit. Applicant is not aware whether the constructions shown in these latter patents have been implemented or tested.

In general, a great number of other considerations affecting blood flow and biological compatibility must be addressed in the construction of any particular blood pump, and the choice of providing magnetic drive and bearings may arise at a late stage in the pump design, after one or more mechanically-suspended prototypes have been tested and the overall size, shape, speed and other characteristics of a pump mechanism have been determined. This piecemeal or iterative approach, while perhaps necessary in the complex and highly risky field of designing machines for in vivo blood handling, may result in designs which are suboptimal in one or more respects. In particular, it may result in a heavy or cumbersome construction, or one which dissipates excessive heat or has an unduly complex control system. Accordingly, there is a need for a simple and effective magnetically suspended blood pump, and for a dependable pump driver.

SUMMARY OF THE INVENTION

The invention addresses these needs by providing a blood pumping and pump drive system wherein a housing defines inlet and outlet ports, and a rotor is suspended in the housing and stabilized to maintain gaps entirely around the rotor and thus prevent damage to pumped blood as the rotor turns. A first set of permanent magnets carried partly in the rotor and partly in the housing passively maintain radial centricity about a central axis, and the rotor is driven by a magnetic coupling to rotate about the axis. Other degrees of freedom are controlled to stably suspend the rotor without mechanical bearings. In one embodiment a second set of magnets are adaptively driven by a set of coils to rotate the rotor and also maintain axial height alignment, and may correct wandering or motion in other degrees of freedom. The coils are carried in a separate drive unit which fastens to the housing and interacts with the second set of magnets to produce both axial force and, independently, rotational torque. In a preferred embodiment, a controller drive unit varies the axial force within a continuous range centered at a neutral position-maintaining force by shifting the phase of signals applied to the drive coils, while pump rotation speed is controlled by changes in frequency of a drive signal. In another aspect of the invention, the rotor body is a cap-shaped body which rotates within a closely fitting housing, and a blood inlet provides blood to the center of the cap so that rotation of the rotor carries the blood over a pumping surface and imparts centrifugal energy to the blood. The rotor is suspended in space, out of contact with the housing, and is positioned in the blood flow path such that blood contacts and flows along both sides of the rotor. A gap defined between the rotor and housing is shaped so that the pressure differential between center and periphery of the rotor permits a counter-flow of blood over the non-pumping surface of the rotor, and results in a pressure distribution which varies as the rotor is shifted or displaced. The pressure distribution engenders a restoring force against the rotor surface in a direction to counteract instabilities as the assembly moves.

In the preferred embodiment, the pump has a symmetric multiple pole magnetic rotor, and the drive system employs a coil arrangement in the driver, with the respective fields of rotor and coils engaging when aligned across a flat disc-shaped stationary engagement surface. When the coil magnets are used to correct axial position or tilt, a plurality of sensors detect the axial displacement of the rotor at one or more points about its periphery and develop a control signal for determining an axial force correction to be applied to the rotor. The controller implements this correction by producing a phase shift in the drive signal. Separate tilt control magnet coils may be provided at the periphery. The driver may also be attached to drive a conventional mechanically-suspended blood pump that has a multiply-poled magnetic rotor. In that case it drives a set of coils located in a driver housing that couples adjacent to the rotor to electromagnetically drive the rotor of such a pump. In that case, phase adjustment of the drive signals is not necessary for axial positioning, although in some control regimens it may be applied to progressively advance the rotor speed, moving between different drive frequencies.

In various other embodiments, additional sets of permanent magnets are provided to reduce instabilities in an axial or tilt dimension, or the rotor and pumping cavity are shaped to hydrostatically control rotor displacements not otherwise stabilized by the magnetic arrangement. By using one or more pairs of solid or cylindrical shell magnets having a common center axis, and aligning the pairs so they are radially nested or lie in adjacent but axially displaced planes, all but one degree of freedom may be passively stabilized by the magnets alone. In various arrangements additional magnets are positioned at the ends of axial or radial torque arms, with their fields aligned to respond to small displacements, to provide effective torque to stabilize the rotor with small or weak magnets without introducing an inertial burden. Hydrostatic control is particularly effective for axial and tilt displacements.

BRIEF DESCRIPTION OF THE DRAWINGS

These and other features of the invention will be understood from the following description and the drawings herein of illustrative embodiments, wherein.

DETAILED DESCRIPTION

Figure 1:
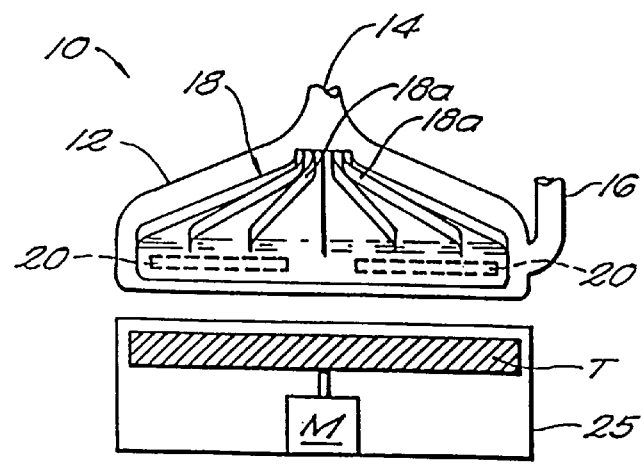
FIG. 1 shows a prior art blood pump.

FIG. 1 illustrates a prior art blood pump 10 of the type used to sustain or supplement circulation, for example, to pump blood to an oxygenator during cardiac surgery. Pump 10 has a housing 12 with a blood inlet 14 and a blood outlet 16, and has a rotor 18 that turns within the housing 12 to propel blood from the inlet to the outlet. As illustrated, the rotor 18 carries a plurality of blades or vanes 18*a* which catch and engage the blood to enhance pumping efficiency. As discussed above, other prior art pumps are available which lack vanes, and instead employ one or more parallel flared or bell-shaped surfaces that frictionally engage and carry the blood while avoiding the turbulence, shear or other physical trauma to blood cells which might be caused by a more abrupt mechanical contact. In each case, however, the pumping element rotates in the blood path to sling the blood outwardly and raise its pressure to achieve pumping. As further illustrated, a drive unit 25 magnetically engages a plurality of magnets or plates 20, which are shown in phantom embedded in the floor of the rotor, in order to rotate the rotor. The drive unit may be, for example, a multipole magnetic turntable T driven by a variable speed motor, or an arrangement of magnets carried by a nonmagnetic turntable, which is brought into close proximity so that it magnetically couples the turntable to the fields of the magnets 20 mounted in the impeller, and which is then turned by a separate motor M to cause the impeller to rotate synchronously therewith.

Figure 1A:
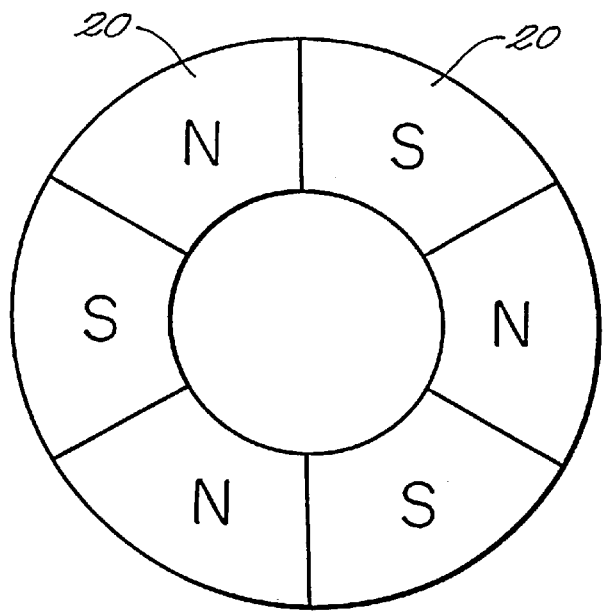
FIGS. 1A and 1B illustrate driver magnets in the impeller of the pump of FIG. 1.
Figure 1B:
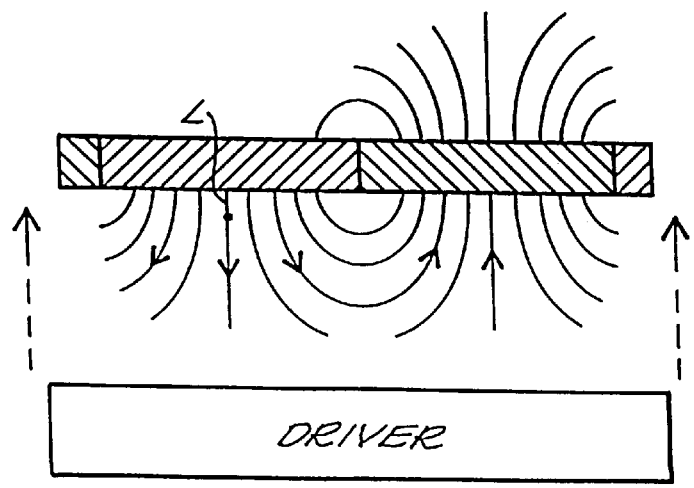

FIGS. 1A and 1B illustrate a top schematic view of the prior art pump of FIG. 1 and a vertical chordal section through its magnets, respectively. As shown, a plurality of magnets 20 are arranged as successive portions of the disc area. Each magnet 20 of the six-pole ferrite assembly embedded in the rotor 18 is a pie-sliced arcuate segment or region, and the magnets are poled N–S in the axial direction (vertically, as shown in the FIGURE) with the six segments alternating in polarity. The side view, or chordal section, FIG. 1B schematically shows the magnetic field pattern near one pair of magnet poles. The axial component, which is vertical in this figure, falls off with distance from the magnet face, and in one device has a value of approximately 70 mT in the central portion of the pole face at a distance of 0.14", which corresponds roughly to the closest feasible spacing for mounting of an external driver disc. The magnetic field lines allow a magnetic coupling to be achieved over substantially the full area of the impeller base by the expedient of providing a complementary pole pattern (e.g., an identically-poled disc shifted by $\pi/6$) in the driver 25 (FIG. 1). When such a driver disc 25 is placed parallel to the magnets 20, the drive "locks on" to the impeller causing the impeller to move in synchrony with the driver.

Figure 7A:
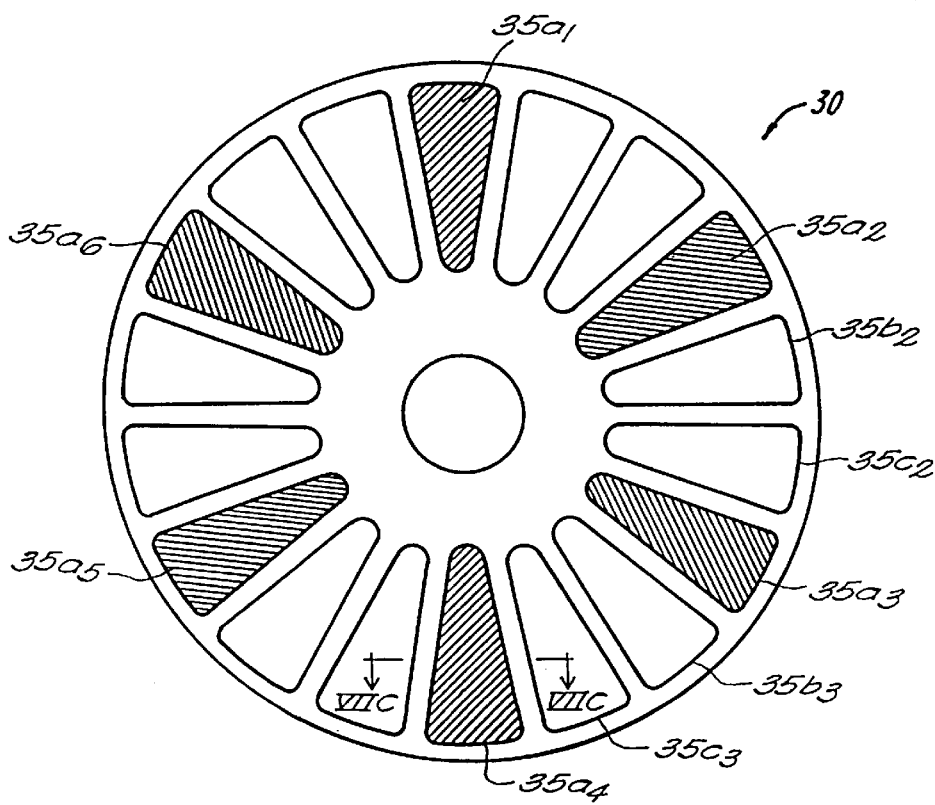
FIGS. 7A–7C illustrate a drive unit and simplified driver useful with prior art pumps.
Figure 7B:
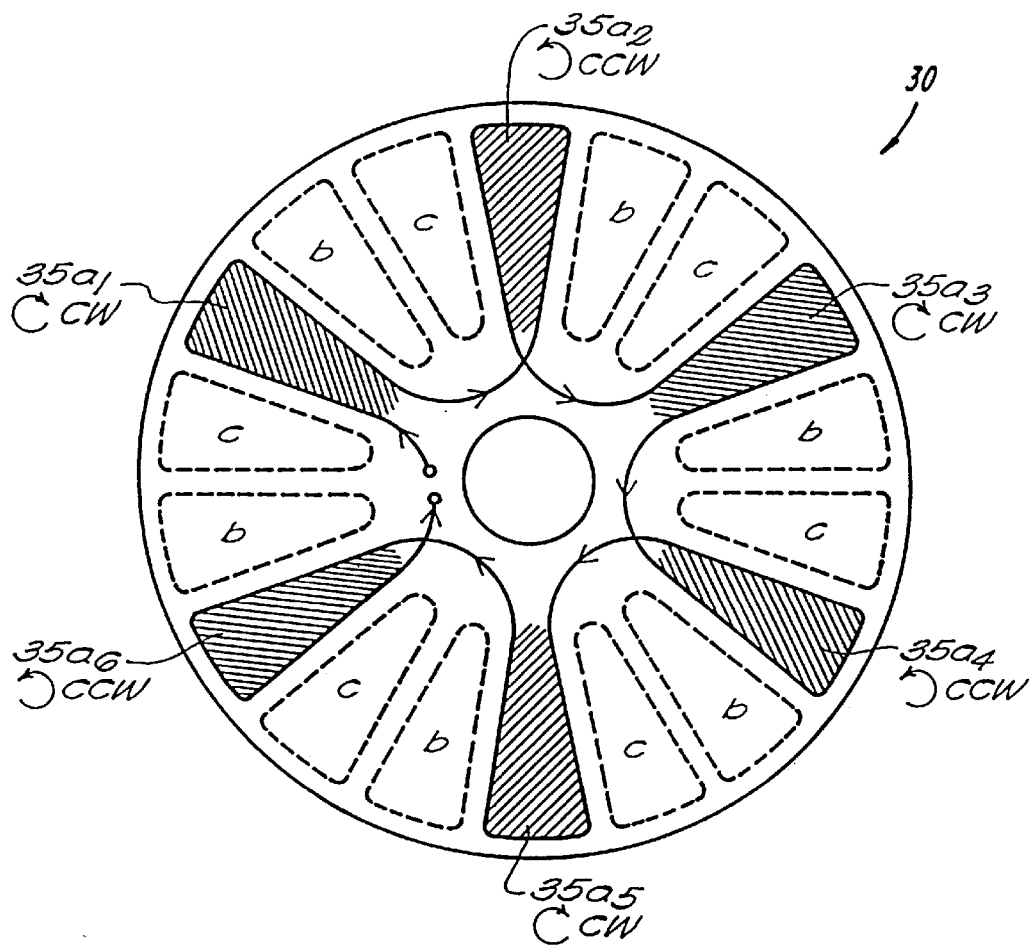
Figure 7C:
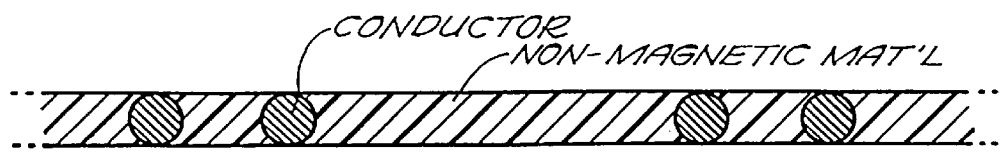

In accordance with one aspect of applicant's invention, an electromagnetic driver is provided for a magnetic pump rotor, which may for example be the prior art rotor 18, to drive the rotor with a stationary pattern of electrical signals. The driver has a plurality of coils with windings extending in a generally radial direction and lying in a plane which is positioned parallel to and closely adjacent to the bottom of the pump. FIGS. 7A–7C illustrate such a drive unit 30.

The drive unit 30 is shown in an embodiment configured to fit the prior art pump of FIGS. 1–1B and provide control of rotational speed and drive torque of that pump. As shown in the top view, FIG. 7A, the driver 30 has a generally disc-shaped active surface which is substantially of the same diameter as the magnetic disc rotor 18 of the pump 10. Disposed over the disc are a plurality of coils arranged in eighteen equi-spaced current windings 35 each extending along a winding path connecting two essentially radial lengths defining the sides of a wedge segment. As shown, the number of these coils is a multiple of the number of poles of the pump rotor 18. The prototype driver was built for actuation by a three phase AC signal, and the eighteen coils were arranged in three groups of six denoted by subscripts "a", "b", and "c", in the FIG. 7A with each phase group comprised of a single continuous strand of twenty-six gauge copper wire that constituted every third current loop of the set. Thus, each phase current winding forms six pie-shaped radial current loops each spaced $\pi/6$ radians apart around the disc, and each spanning one-third of a magnet segment 20.

FIG. 7B illustrates the winding pattern of the coils $35a_i$ of one phase, the "a" phase. As shown, the segment coils of the winding arc each spaced sixty degrees apart around the disc, and current in each segment passes through a radial outward and a radial inward straight path along the sides of each coil. In each successive coil, the radial legs are reversed, with coils having clockwise and counter-clockwise current paths alternating successively around the disc. It will be understood that when the driver is coupled to the pump, each winding segment at any instant will lie below a permanent magnet (20C FIG. 1A) of opposite polarity to that of its neighbors. Since the coil current direction is opposite in each adjacent pair, a unidirectional drive force is established by the entire "a" winding, coupling to each of the six magnets 20 in the same sense over the entire rotor drive surface. A similar winding pattern is applied to the "b" and "c" windings, which are each shifted by an additional $\pi/9$ radians. With this configuration, by applying a three phase drive signal to all three windings in the standard commutation sequence for a brushless DC motor, the disc impeller of pump 10 is reliably driven by the driver 30. Details of torque calculations and drive parameters are readily computed with standard models as set forth, for example, in D.C. Hanselman's book *Brushless Permanent-Magnet Motor Design* (1994. New York: McGraw Hill). Simple power supplies to run the driver are readily built with off-the-shelf items, as described in Philips Semiconductors, *Data Sheets for Full-Wave Sensorsless Drive ICs for Brushless DC Motors*, 1994.

In accordance with a further aspect of applicant's invention, a blood pump is not only driven by a separate drive having electromagnetic coils embedded in a non-magnetic flat face, but the pump itself has an at least partially magnetic suspension which both suspends the rotor and drives it within the pump housing free of any direct physical contact between the rotor and the surrounding housing.

Figure 2:
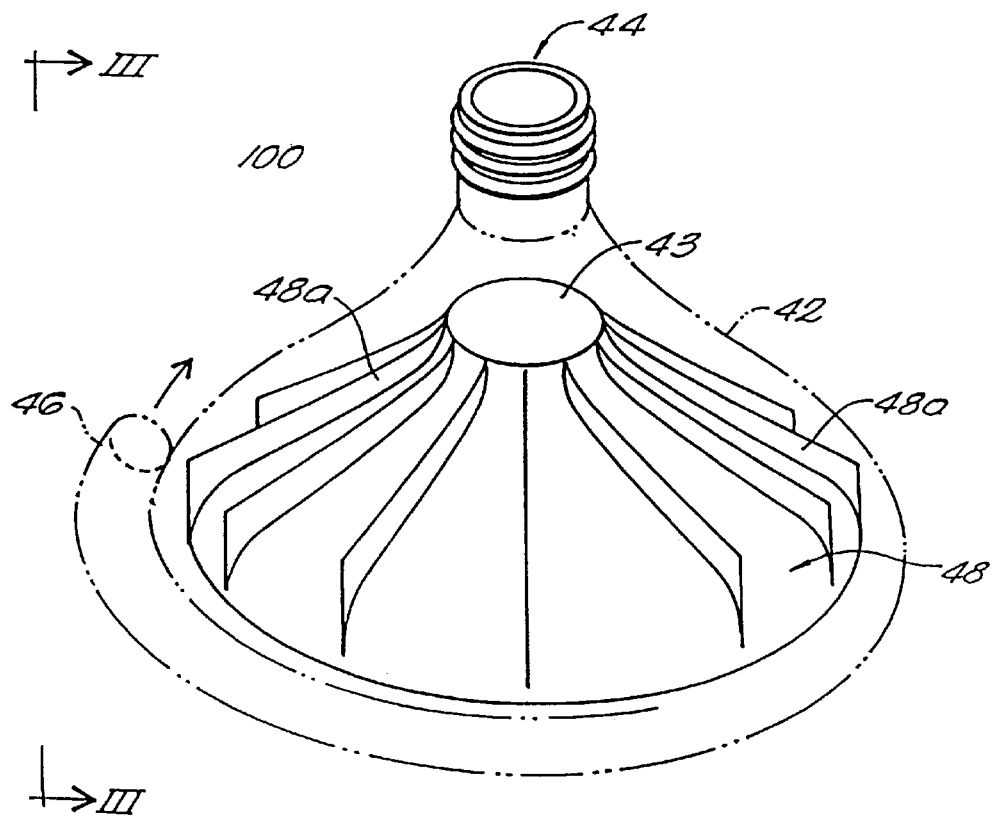
FIG. 2 illustrates a first embodiment of a pump in accordance with the present invention.

FIG. 2 illustrates a blood pump 100 in accordance with this aspect of the present invention. Pump 100 has a housing 42 with an inlet 44 and outlet 46, and has a rotor 48 for pumping blood from the inlet to the outlet. As for the pump of FIG. 1, a plurality of vanes 48a on the rotor engage the incoming fluid to spin it to the outer peripheral region, increasing its momentum as the blood moves from the inlet to the outlet.

The housing 42 of this embodiment has the general shape of a broad, low-peaked Erlenmeyer laboratory flask, with the impeller body 48 substantially filling a flared chamber formed by housing 42. A post or nub 43 extends up from the floor of the housing at its center, and the impeller body 48 mounts like a hat over the post so that it is centered in the housing and the bottom of the impeller is positioned just above the floor of the housing. Significantly, while the rotor/impeller 48 fits over the post, it does not contact the post 43, but has a gap 43a therebetween, which is maintained by a set of nested cylindrical magnetic bearings which exert a mutual radially-directed repulsive force to keep the rotor centered and prevent contact.

Figure 3:
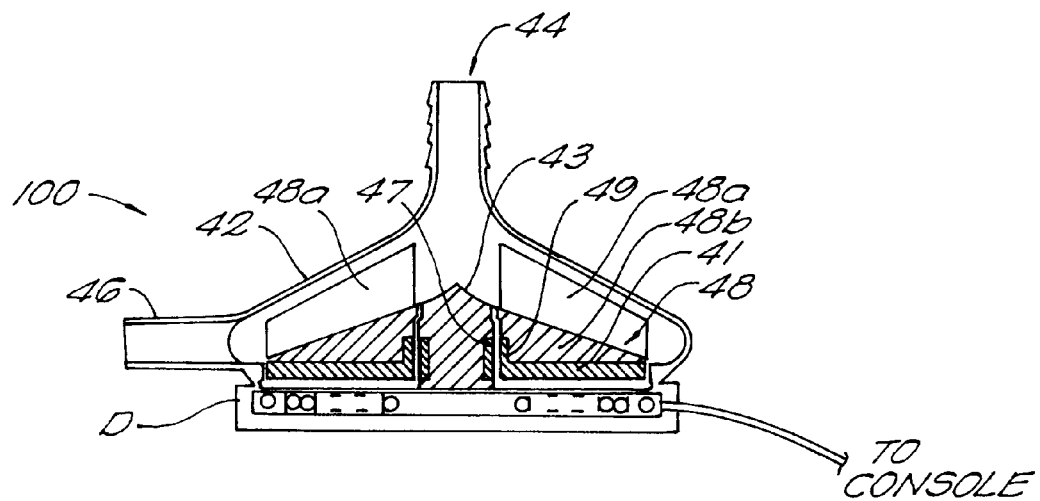
FIG. 3 shows a section through the pump of FIG. 2.

In accordance with one principal aspect of applicant's invention, the rotor is suspended in a self-centering frictionless magnetic bearing formed by inner and outer permanent magnetic cylinders which may for example be radially poled and of opposite polarity. This construction is further illustrated by FIG. 3, which shows a section through pump 100 in a plane containing the axis of pump rotation. As shown, the rotor is symmetric and annular, surrounding the post 43. A cylindrical permanent magnet 47 forms a collar or band about the post 43, while another cylindrical magnet 49 of slightly greater inner diameter than the outer diameter of magnet 47 is fitted like an inner bushing to form a magnetic cylinder surrounding the central bore of the rotor 48. As shown, however, magnet 49 does not contact the post, and in fact it preferably lies across a gap and beneath a biocompatible surface coat 49a. As in the prior art pump, the floor of the rotor has plate-like permanent magnets, or a single plate with corresponding magnetically-poled segments, 41 secured therein. The magnets or segments 41 have a pole pattern for example, as illustrated in FIG. 1A. A driver unit D is shown in FIG. 3 mounted to the pump 100 below its floor. Unit D is an electromagnetic driver as described above in connection with FIGS. 7A–7C, and so far as the rotational drive is concerned, magnets 41 and the driver may operate similarly to the embodiment of FIGS. 7A–7C to rotationally drive the rotor.

Significantly, however, since pump 100 maintains its radial centricity by a noncontact magnetic bearing, the impeller is thus free to move axially, and the bearing is, in fact, axially unstable so that the rotor might travel or oscillate unless a set of balanced axial forces were maintained. This instability is addressed in accordance with several different aspects of the invention as described below, by one or both of the steps of changing the drive current phase during operation of the driver D to introduce a corrective axial force, and providing a self-adjusting flow path formed in opposing sides of the rotor/housing spacing that introduces a corrective force distribution to counteract displacements such as rocking or axial displacement, i.e., by a fluid-stabilized rotor design.

Figure 3A:
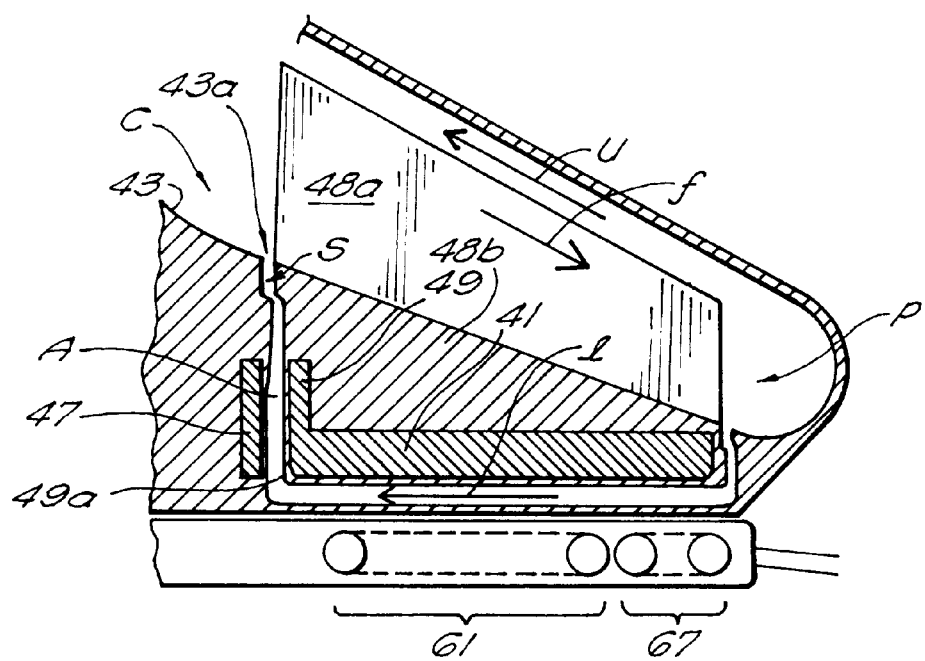
FIG. 3A is an enlarged detail thereof illustrating flow.

Details of rotor suspension and its stabilization will be better understood from an examination of the enlarged partial sectional view of FIG. 3A. Rotor 48 is formed of a generally solid annular body 48b, which has a plurality of impeller vanes 48a that extend upwardly as shown from solid body 48b to a height such that the body and vanes substantially occupy the entire cross sectional area of the housing interior, with only small gaps remaining between the rotor and housing. In common with existing pumps, flow is created by providing inlet blood at low pressure to central region c, and transporting the blood in a turning path captured by vanes 48a so that it acquires kinetic energy as it is driven rapidly along a flow path f parallel to the moving vanes acquiring a tangential velocity at an exit manifold or passage p of higher pressure fluid extending around the pump periphery. The rotor 48 is sized so that a fluid-filled gap surrounds all sides of the rotor, and the pressure differential between outlet region p and inlet region c creates a counter flow of fluid along an upper fluid return path, denoted by the arrow u in FIG. 3A, and a lower fluid return path l, both of these paths running from the high pressure periphery of the pump rotor back to the low pressure center.

In operation the cylindrical magnets 47, 49 produce a sufficiently high repulsive force across the small gap A therebetween that the rotor remains substantially centered about the post 43. However the rotor is free to rise or fall vertically, by a distance equal to the sum of the upper and lower gaps, in response to impact or acceleration of the housing, to flow or momentum changes, or to other dynamic changes and perturbations. The central axle 43 is constructed to form a through passage at gap A between the magnetic cylinders that varies as the rotor shifts axially and introduces a compensating vertical lift force due to the altered flow.

In the illustrated embodiment this is achieved by providing a post 43 and central rotor bore which each vary from straight verticality by having a purely cylindrical surface portion located at the magnets 47, 49, and an offset or stepped portion s near their upper region which defines a progressive occlusion of the lower return flow path l as the rotor descends. With this configuration, lowering of the rotor causes an increase in pressure experienced along the lower surface of the rotor bounding the return flow path l, and this circulating return pressure exerts a compensating increase in vertical force to lift the rotor. This flow pattern further washes the non-pumping surface regions of the rotor with a continuous flow of fluid, and thus prevents occurrence of dead spaces or flow pockets below the rotor in which thrombic accumulations might arise. Thus, by providing a central flow gap between the inner and outer centering bearings 47, 49 applicant eliminates dead-ended or stagnant recesses that are a limitation of prior art constructions.

The rotor 48 is formed of solid body material in region 48b, which may be the same material as vanes 48a and is preferably a biocompatible polymer, and has magnetic material in the magnet poles 41 which is in general ferritic and of greater density. The magnets may be very high strength compact (e.g., low total mass) magnets, so that the density of the major portion of the body may be selected in a range suitably low so that the rotor has an average density near that of blood. This makes the rotor effectively weightless when suspended in or surrounded by the fluid, rendering operation of the pump independent of housing orientation, and of gravity and also substantially uninfluenced by accelerations of the pump housing. In particular, hydrostatic suspension in this manner may alone control the axial suspension of the rotor, or if desired may be used to correct perturbations to a relatively small magnitude, with a further axial correction then being effected, for example, electromagnetically with a driver as illustrated in FIGS. 7A–7C.

Advantageously, the driver when acting on a pump of the present invention may not only rotate the pump, but may be controlled to introduce an axial force. This is accomplished by providing the coil drive current in phased relation to the passage of the rotor thereover, with a phase delay calculated to produce the desired magnitude of axial correction force.

Figure 4A:
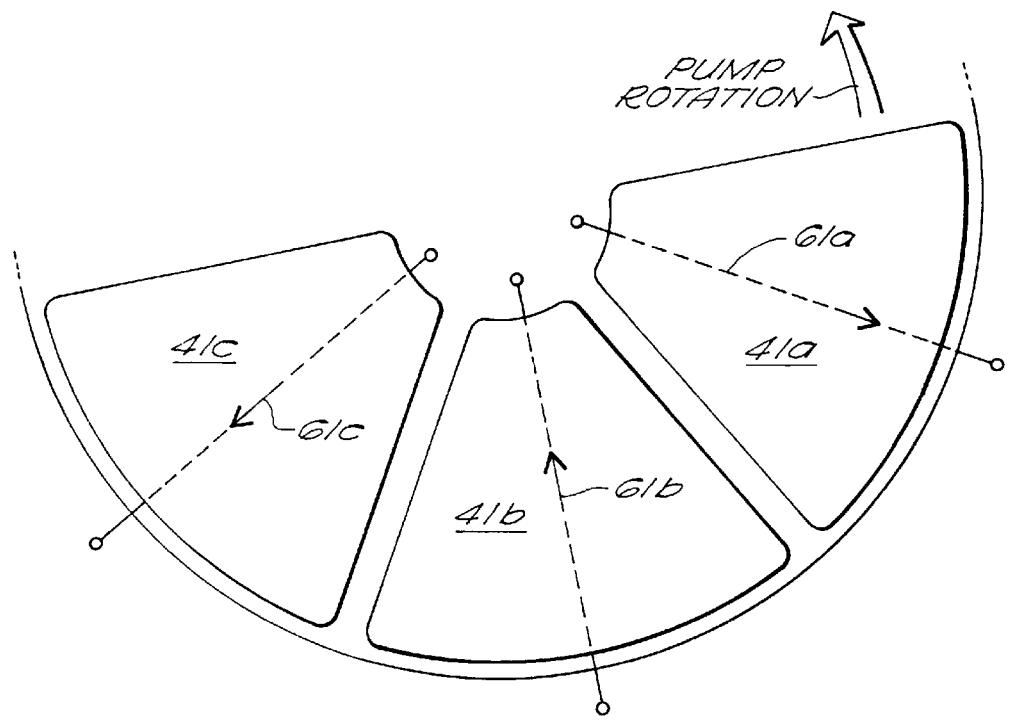
FIGS. 4A–4C show drive forces as a function of the phase of a drive signal.
Figure 4B:
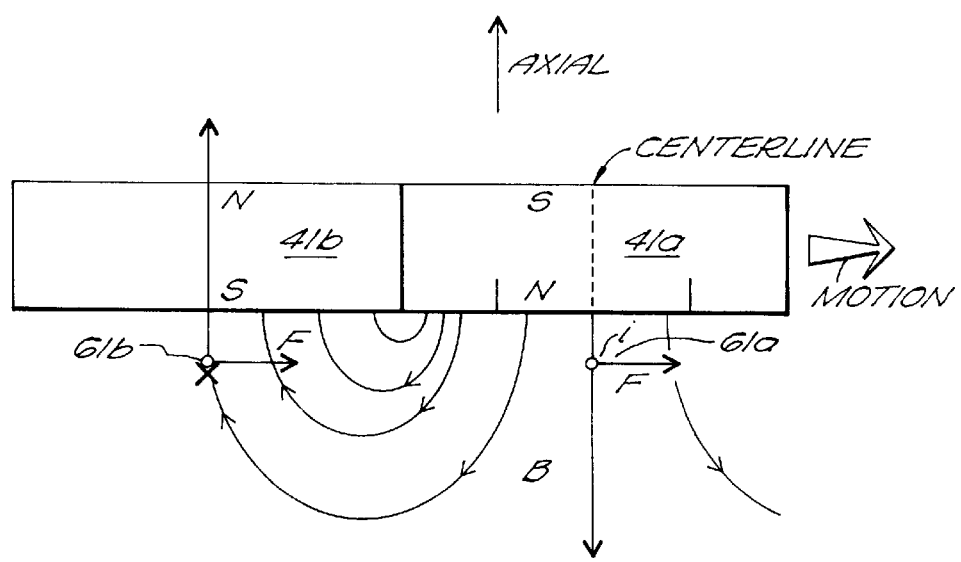
Figure 4C:
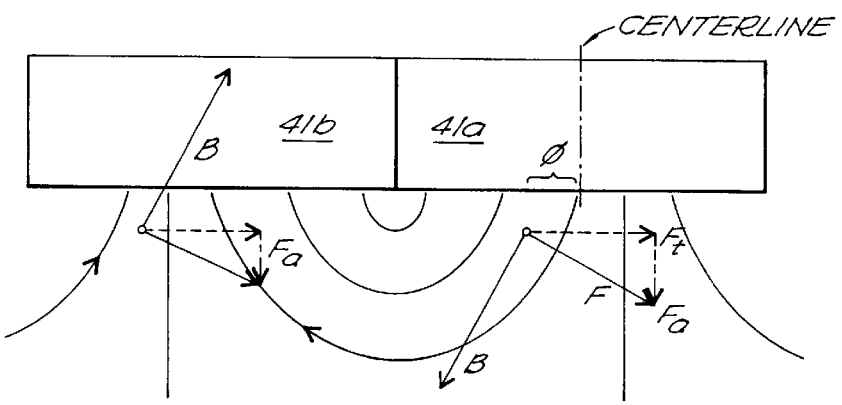

FIGS. 4A–4C illustrate this operation. FIG. 4A illustrates in schema the magnet segments 41 of the pump rotor, and a single conductor 61a, 61b, and 61c of a driver under each segment, with the conductors 61 extending along a straight radial path below the rotor. The current direction in each wire 61 is indicated by a direction arrow.

FIG. 4B shows a vertical section through the magnets 41a, 41b and conductors 61a, 61b illustrating the interaction of the magnetic fields of the moving rotor and the induced field B of each conductor due to drive current j. As shown, the adjacent permanent magnets 41a, 41b are poled vertically but in opposite sense, and have a pure axial (vertical) field at their midline, with the field angled progressively more toward the edge of each magnet segment. The net force F on the rotor segment 41a as a segment midline passes over the conductor 61a having a current flow j in a direction outward from the plane of the drawing is the same as that exerted by the opposite flow in conductor 61b under the adjacent magnet, and is tangential to the rotation, i.e., perpendicular to the conductor.

FIG. 4C shows a similar force diagram for the rotor 48 after the centerline of each magnet segment 41 has passed the conductor 61 by an amount Ø. In this case, magnetic field of the conductor interacts with the inclined field of the segment to produce a force F having a component $F_r$ tangential to the rotation as well as an axial component $F_a$, which as illustrated is a downward force for this direction of current flow. Similarly, by actuating the conductors 61 before the magnet centerline is in overhead alignment, a net upward axial force is exerted on the rotor. In this manner the phase of the signal in a set of radial conductors 61 applies vertical forces for controlling vertical position of the pump rotor.

Applicant has determined that an effective level of force may be exerted by such controls, without dissipating excessive heat energy or otherwise producing conditions incompatible with blood pumping. Moreover, all or portions of the windings of the driver as shown in FIGS. 7A and 7B may be used to provide drive current for simultaneously controlling both the axial force and rotational drive force applied to the rotor.

Figure 5:
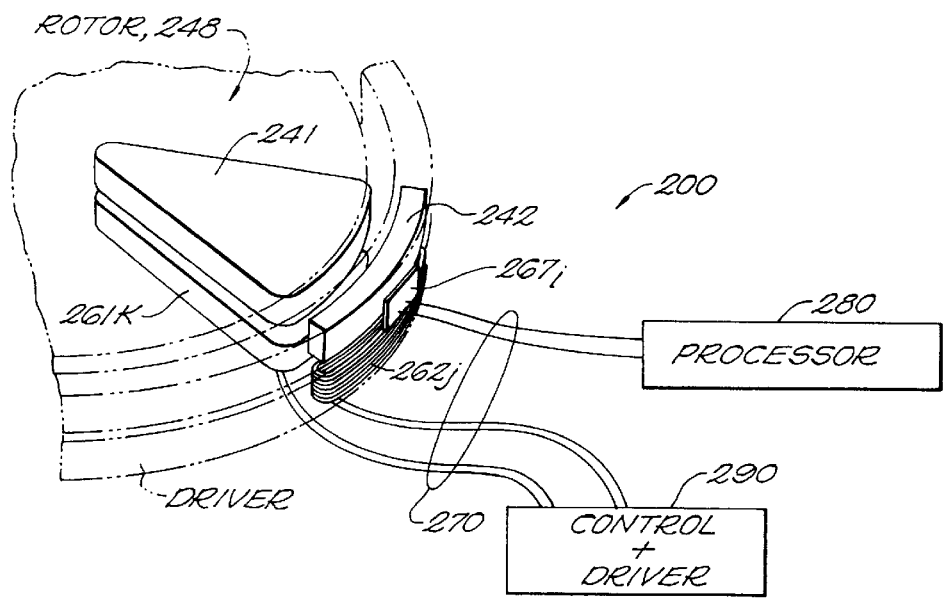
FIGS. 5 and 5A illustrate the pump and driver system of the present invention.
Figure 5A:
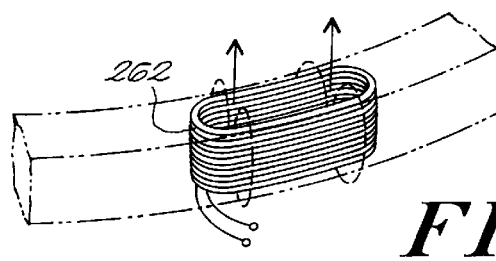

FIGS. 5 and 5A show a control system of one embodiment 200 specifically configured for so controlling axial position.

As shown, system 200 includes a pump having a rotor 248 with embedded segments of permanent magnet 241 as described above together with a further set of magnets 242 located circumferentially about the periphery of the impeller for enhancing their moment arm about the center point of the rotor. The drive unit D' of system 200 includes a first set of coils 261 substantially like coil 61 previously described, and in the illustrated embodiment also contains a second set of coils 262 which are a set of circumferentially oriented toroidal windings positioned to exert a vertical force locally in the peripheral band of the rotor containing the magnet or magnets 242. Equi-spaced around the circumference of the driver are three or more Hall sensors 267 which sense the proximity of the magnet(s) 242 rotating overhead and provide sensing signals to a control or processing circuit which uses these position signals to determine the degree of tilt of the rotor within the housing around each of two independent tilt axes laying in the plane of rotation. The current provided to windings 262 is then made proportional to the desired axial force to correct tilt of the rotor as the corresponding magnets 242 pass over the coils 262. A common wiring harness 270 carries the leads from the position sensors 267$_i$ and the control or driving currents provided to the various coils used for axial height correction and two axis tilt correction. In addition to the peripheral magnet(s) 242 shown in FIG. 5 one or more magnets or magnetic domains of specific width or sequence of widths may be provided to provide a synchronizing pulse or pulse train to the sensors 267 for identifying disc rotational position. These signals in turn may be used when necessary, to determine a rate of pump acceleration or deceleration for either determining the load on the pump, or adjusting the drive signals to accommodate a sensed load, or for moving between different rotational speeds.

As shown in FIG. 5, harness 270 connects the channel signals of the position sensors 267$_i$ to a processor 280 which determines the tilt of the rotor. Preferably sensors 267$_i$ and separate magnets 242 are arrayed symmetrically around the rotor such that the magnitude of opposed pairs of sensors 267 may simply be compared in a bridge and the resultant sum passed to a logic array to determine the direction and relative magnitude of tilt along two independent directions. Alternatively, more complex signal processing may be applied by a microprocessor as known in the art for gyroscopic or motor position sensing. Processor 280 then converts the sensed axial position and tilt data to power and timing control signals for a control and driver unit 290 which provides power to the current windings of the magnets 261, 262 of the channels.

As noted above, the phase of the current signal or impulse provided to the conductors 261 determines the magnitude of the net axial and rotational forces exerted thereby on the rotor. The discussion above has assumed for simplicity a three channel winding pattern wherein each channel has a coil wound about six equi-spaced driving segments to both turn and axially correct the rotor position. This arrangement works with a standard brushless motor electronic drive commutation system as is commonly used for brushless motor drives in other fields. As described above, by simply changing the phase of the drive signals, the axial force is controlled in accordance with the signals from the average axial height sensors 267, while tilt corrections are accomplished with peripheral coils and magnets.

In other embodiments, tilt correction is accomplished using the same pie-shaped coils as the rotational drive components. To do this, each of the drive segments of a given channel is separately powered so that the axial force exerted in one angular segment differs from the axial force exerted in adjacent or opposite sectors. The control program is modified to simultaneously apply the correct total vertical force for axial control, but the force is non-uniformly distributed around the circumference when tilt is detected, in a way that varies with angular position to compensate for the tilt of the rotor. In that case, the processor 280 may include a microprocessor having more complex signal processing abilities and incorporating suitable algorithms for detecting mutation or instabilities, and for applying appropriate control laws to stably maintain pump rotation while damping or eliminating the sensed disturbances of the rotor alignment around the in-plane tilt axes and variations in vertical position. Thus, in further embodiments, the invention contemplates the provision of a drive mechanism having one, or more than one set of coils, and having a controller which simultaneously controls axial position as well as tilt of the rotor while providing rotational drive force to maintain the selected pumping characteristic, e.g. speed, flow rate or pump output pressure.

The foregoing construction advantageously places all the electromagnets of the pump construction on one side of the rotor, conveniently located in a bayonet-mount disc-shaped drive unit below the housing, thus allowing simple and fast removal or installation of the pump head. The pump head itself—that is, the rotor and its housing—is a simple assembly of molded plastic parts with embedded permanent magnets. This may be manufactured as a single piece rotor surrounded by two interfitting pieces which are joined together to form the housing, thus constituting a relatively low-cost disposable subassembly. The electromagnetic coil driver advantageously has no moving parts, enclosing only a plurality of current windings and the Hall effect sensors (if used) as described above.

As shown in FIGS. 3 and 3A, the concentric permanent cylindrical magnets 47,49 passively achieve radial centering of the rotor suspended in free space, so only the other degrees of freedom require active control, and these may in part be corrected passively by hydrodynamic pressure applied to the upper, lower and inner flow lift surfaces of FIG. 3A, by application of axial forces through the current windings of the driver, by tilt corrections through the same or separate magnets, by a doublet or triplet configuration of magnets to stabilize the verical spacing, or by combinations of the mechanisms described above. However, it should be noted that the radial centering bearings, whiled referred to as cylindrical, need not be overlapping concentric cylinders. Indeed it will be apparent that the centering spindle or post 43 of FIG. 3 may include a solid cylindrical rod magnet rather than the hollow cylinder or collar 47, and a consideration of the possible configurations with simplest axial or radial field orientations of the magnets reveals a number of combinations in which pairs of magnets having a common center axis may achieve stability or stable bias in one direction either while lying in axially offset planes, or while being radially nested in a common plane. Thus, the terms concentric or coaxial are understood to mean simply that the two magnets share a common central axis, but they do not necessarily lie in the same plane.

Indeed, in other embodiments, the radial centering bearings may be positioned slightly offset, or with their fields arranged at an angle, and these may be arranged to provide a net axial force. In this case, a second set of permanent magnets may be embedded in facing surfaces of the rotor and housing, respectively, to counteract the non-zero but constant axial force bias introduced by the radial suspension. Such an arrangement has the advantage of utilizing the asymptotic increasing forces between each of two sets of magnets and is therefore able to stabilize the rotor in a central position in a second or third dimension. Furthermore, by employing relatively small magnets located near the extreme height or outer edge, a large torque arm may be provided to act in one direction with relatively little weight penalty in the rotor. Alternatively, rather than passive stabilization with multiple sets of magnets, the axial force for correcting a fixed axial bias of the permanent magnet suspension may be provided by the electromagnetic driver, in the same manner as discussed above. Such an arrangement may utilize driver control protocols that start from a resting state position in which the rotor is biased in one direction, so that only a small electromagnetic adjustment is necessary to supplement the axial force components introduced during operation by fluid pressure against the rotor. Thus, under actual pumping operation the controller may be made to more quickly achieve a stable state at lower coil currents, or operate with otherwise enhanced control characteristics.

Figure 8:
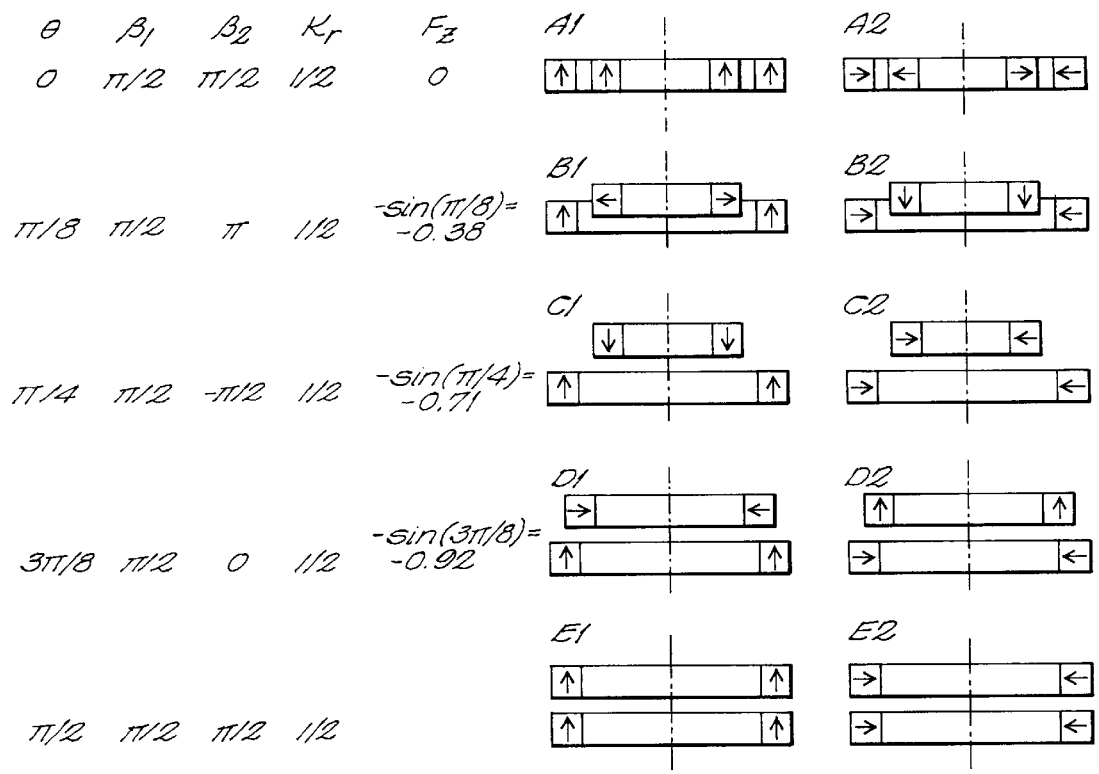
FIG. 8 illustrates passive radial control, permanent magnet configurations.

FIG. 8 shows the ten possible configurations $A_1, A_2 \ldots E_1, E_2$ for the permanent magnet radial bearings, if a pair of magnets are restricted to being either axially or radially magnetized. In this case, the orientation of the housing and rotor magnets $M_1, M_2$, i.e. the angles $\beta_1, \beta_2$ of their magnetization vectors $J_1, J_2$ (using Sommerfeld notation), can take only the values $0, \pi/2, \pi$ or $3\pi/2$. For the radially nested concentric case (denoted $A_1$ or $A_2$ in FIG. 8) where the angular displacement $\theta$ between $M_1$ and $M_2$ is zero, there is no axial force. Otherwise, where $M_2$ is displaced at a non-zero angle $\theta$ from $M_1$, there is a nonzero axial force component $F_z$. All ten configurations produce comparable levels of radial stiffness $K_r$, but the arrangements $B_1 \ldots E_2$ with an angular offset between the two permanent magnets all produce a fixed component of axial force. As noted above, this component is preferably counteracted by any one or more of three mechanisms: other sets of permanent magnets, compensating electrical currents in the drive and control magnet conductors, or fluid pressure forces acting on the rotor.

Figure 6:
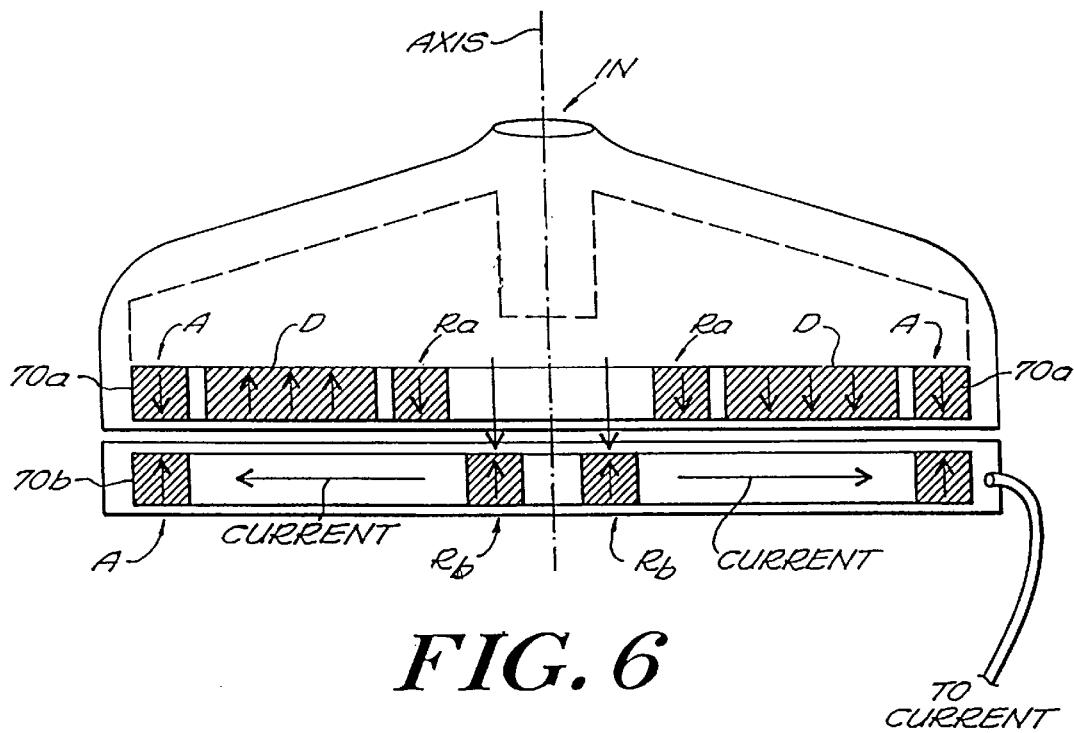
FIG. 6 illustrates another embodiment of the invention.

A second set of permanent magnets may also be provided to control the "tilt" or angular deviation of the rotor from the housing axis. FIG. 6 shows an embodiment with such tilt control, illustrated in a cross-section similar to the view of FIG. 3A. In this embodiment the radial centering magnets, denoted $R_a, R_b$, have the relative position and magnetization of the configuration schematically shown as $C_1$ of FIG. 8, while a second magnet 70a is provided extending in an annulus about the periphery of the rotor disc, with a corresponding magnet 70b located in the plane of the driver. In this FIGURE, the radial position control bearings are denoted by R and the angular tilt control bearings by A. Two opposite permanent magnet drive segments D, and the current sense in the drive coils are also illustrated. Here, there is a net axial attraction between the two "R" magnets, and a repulsion between the "A" magnets. The strong increase in repulsion as the gap decreases, together with the long torque arm provided by positioning the "A" magnets at the outer periphery, effectively prevents excessive tilt, but since there remains an axial instability this latter degree of motion must still be corrected, preferably by hydrostatic force from self-restoring fluid pressure rotor design as shown in FIGS. 3 and 3A, or by phase control of the driver coils, as described above.

While cylindrical permanent magnet arrangements are used for the radial position constraint and may be arranged to correct other displacements, the present invention contemplates a number of preferred constructions which differ for a purely axial permanent magnet (PM) suspension and for a suspension that controls additional degrees of freedom.

For initial prototyping of a free-rotor pump, the configuration of permanent magnets shown in configuration A1 of FIG. 8 was employed. The results of characterization of this arrangement of magnets are illustrative of the general properties of permanent magnet forces. Two cylindrical rare earth (samarium cobalt) magnets, magnetized axially, were nested concentrically with their magnetization aligned. These magnets were 0.25 inches (6.4 mm) thick with OD 0.375" (9.5 mm) and 0.75" (19.0 mm) for the small and large magnets respectively, and ID of 0.440" (11.2 mm) for the outer magnet. This configuration acts as a radial bearing due to the mutual repulsion of the similarly aligned magnets.

When manipulating the magnets in this radial magnetic bearing configuration, the instability in axial and angular degrees of freedom is even more obvious than the radial stability. When coaxially nested with collinear magnetization, the two magnets have a strong tendency to fly apart along their axis. This trade off between stability in one degree of freedom and instability in others is a consequence of the nature of magnetic and electric fields, as shown by Earnshaw in the nineteenth century. It is not possible to arrange static magnetic fields in a way that a magnet is stably suspended in all degrees of freedom. The consequence for arrangements of permanent magnets is that introducing stability in one degree of freedom creates at least as much instability in the other degrees of freedom. To give a quantitative expression, for cylindrical bearings, the axial instability is at least twice as large as the radial stability, since there are two equivalent radial degrees of freedom. This is expressed in terms of force constants as $K_a \geq -2 K_r$, where $K_a$ and $K_r$ are analogous to spring constants: $K_a = dF_z/dz$ and $K_r = dF_r/dr$. A positive value of this constant implies instability, while a value less than zero describes a stable, or spring-like system.

The radial bearing configuration A1 of FIG. 8 is also unstable with respect to the rotations $\theta_1$ and $\theta_2$ about the two orthogonal axes in the plane of rotation. The angular stability constant is defined similarly to the translational one, as the derivative of torque with respect to angle: $K_\theta = d\tau/d\theta$, and for a cylindrical bearing this can be shown by integration around the cylinder to be related to the angular and radial constants as: $K_\theta = R^2/2 \; K_a = -R^2 \; K_r$.

In accordance with a further aspect of the invention, arrangements of permanent magnets are provided to passively stabilize several degrees of freedom of the pump rotor, and in some embodiments by adjusting the relative strengths of the magnet pairs and the torque arms over which they exert their forces, the permanent magnets place all the instability in one degree of freedom. In that degree of freedom, stability is then provided by a different (non-PM) system of forces which does not introduce extra instability. The non-PM mechanism may be a passive or an active control mechanism.

Figure 9A:
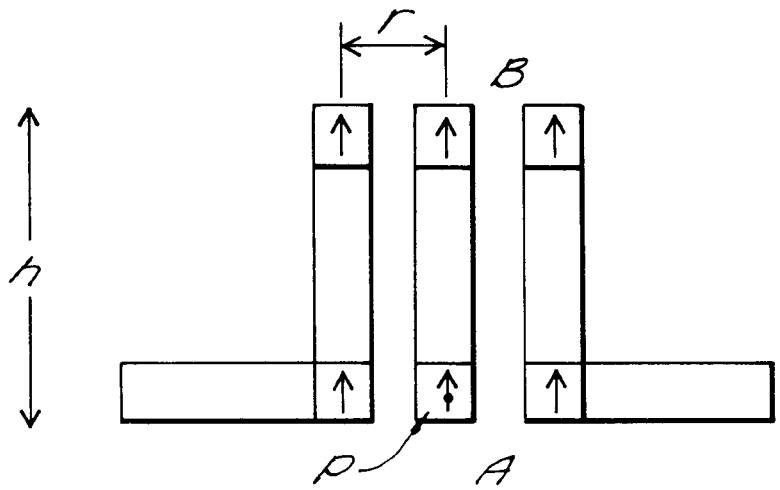
FIGS. 9A–9C illustrate three different permanent magnet radial and tilt control embodiments of the invention.
Figure 9B:
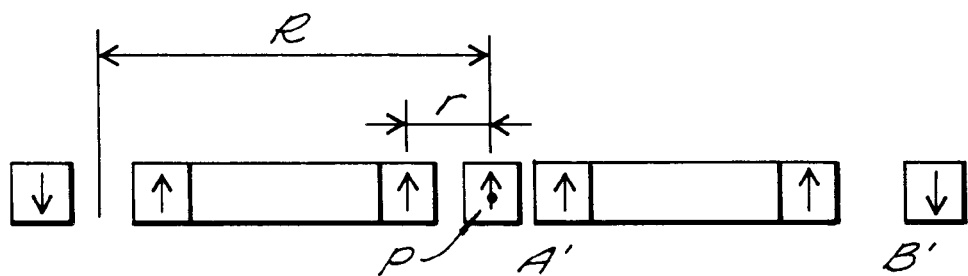
Figure 9C:
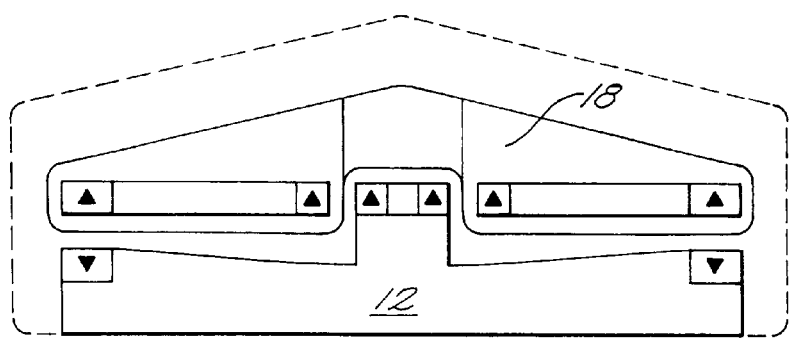

In one of these pump embodiments, magnetic bearings are used to stabilize the rotor with respect to radial and angular ($\theta_1$ and $\theta_2$) displacement, leaving control in the axial direction to other forces. Several arrangements to accomplish this are shown in FIGS. 9A–9C. In the embodiment of FIG. 9A, two pairs of cylindrical bearings of the type described above are stacked with the lower inner and outer pair A of magnets lying below the upper pair B at an axial separation h. The accounting for stability in this arrangement is summarized in Table 1. For bearing pair A, the radial and axial constants are measured, and the angular constant for rotations about the center point P in the lower plane is calculated from $K_\theta = R^2/2 \; K_a$. For bearing pair B, the radial restoring forces acting through the moment arm of length h serve to stabilize the rotor with respect to rotation about P by an amount $h^2 K_r$. The effect of angular instability of bearing pair B about its own center point contributes to the instability of the assembly as a whole to rotation about P only as $r^2 \sin^2\alpha\, K_r$, where $r/h = \tan\alpha$. The net contribution of bearing pair B to angular stability about P is thus $K_\theta = (h^2 - r^2 \sin^2\alpha) K_r$. The condition for overall angular stability is $h^2 > r^2(1 + \sin^2\alpha)$. For the bearing assembly used in a model of the suspended-rotor pump, we chose h=0.45" (11.4 mm) to yield the numbers in Table 1. The numbers indicate stability in all but the axial degree of freedom. In order to suspend this system it is therefore only necessary to supply an axial restoring force characterized by a force constant (stiffness) $K_a < -12.4$ N/mm, without introducing significant instability in other directions.

TABLE 1

Stability of permanent magnet bearing configuration in FIG. 9A

| Bearing FIG. 9A | Radial Force Constant $K_r$ (N/mm) | Axial Force Constant $K_z$ (N/mm) | Angular Force Constant $K_\theta$ N · m/(radian) |
|---|---|---|---|
| A | −2.7 | 6.2 | 0.18 |
| B | −2.7 | 6.2 | −0.26 |
| Total | −5.4 | 12.4 | −0.08 |

Thus, by providing two axially spaced sets of radial bearings, tilt about the axes lying in the plane of rotation is passively controlled without requiring sensors or specialized control circuitry, so that only a corrective axial force need be provided by an extrinsic mechanism to completely correct the suspension. As noted above, this force may be provided by phase-control of the rotational drive coils, or by hydrodynamic lift surfaces and pinch-off contours facing the various blood pumping and return flow surfaces around the rotor.

Another embodiment may include two pairs of cylindrical permanent magnets all of which are concentric and lie in the same plane. FIG. 9B shows such a configuration. In this embodiment a central bearing pair A consists of inner and outer cylinders having parallel axial magnetization, while an outer bearing pair B includes a cylinder mounted in the rotor periphery which rotates within a surrounding cylinder of antiparallel magnetization mounted in the housing. In this case, the inner bearing A is radially stable, and is unstable with respect to axial translation and to rotations $\theta_1$ and $\theta_2$, while the outer bearing set B, a set of cylindrical bearings with their magnetizations antiparallel, is radially unstable, but is stable with respect to axial and angular degrees of freedom. The condition for overall radial stability for this configuration is $K_{rA} + K_{rB} < 0$.

Angular stability requires $R > r(K_{aA}/K_{aB})^{1/2}$ where $K_{aA}$ and $K_{aB}$ are the axial force constants for the bearings A and B, respectively. Overall radial and angular stability are thus ensured by the proper choice of R and $K_{aA}/K_{aB}$.

These two arrangements of permanent magnets exert no net axial force. The invention also contemplates pump suspensions having arrangements of cylindrical permanent magnets that provide net radial and angular stability but also introduce a net axial force. One such pump configuration is shown in FIG. 9C. In this arrangement, the concentric inner set of nested permanent magnets provides radial stability, while the outer rings of magnets, which are mutually repulsive, ensure angular stability. In operation of the pump this axial force will be opposed in one or more constructions by other forces exerted on the rotor by the pumped fluid, by currents in the windings, or by external permanent magnets, as described above.

As explained below and elsewhere in this disclosure, the hydrostatic pressure distribution in the fluid surrounding the rotor may itself provide a sufficient axial constraining mechanism to correct all axial instabilities introduced by the magnetic suspension, and may also serve to stabilize the rotor with respect to the radial rotations. When tipping of the rotor occurs, the flow around the rotor alters so that restoring forces are generated near the side of the rotor that is displaced. The net effect when forces over the surface of the rotor are considered, is that a restoring torque is generated. In some embodiments, this mechanism alone corrects for tipping of the rotor, without the application of a second cylindrical magnetic bearing.

Figure 10:
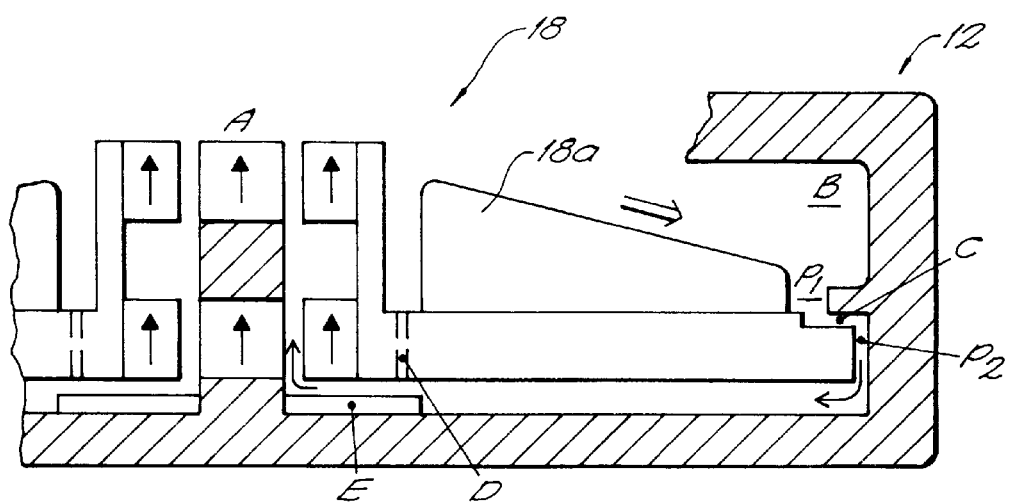
FIG. 10 illustrates a passive hydrodynamic axially controlled bearing useful with the foregoing embodiments.

The hydrostatic balance mechanism for axial control is explained by reference to FIG. 10, which shows a view corresponding to FIG. 3A of a rotor having a PM radial bearing, elucidating details of the flow path around and over the rotor/impeller. The static pressure rises from its low point at the inlet, near A, across the blades on the top surface of the rotor, to a high value, at the outlet, near B. There is a similar pressure distribution on the bottom side of the rotor, and when the system is at equilibrium, the integral of the pressure over the top surface is equal to that over the bottom. There is a washout flow from the high pressure region near B, through the constriction at C, underneath the rotor, through the constriction created by the spacer at E, and back to the central low pressure region. The balance between the average pressures on the top and bottom is governed by the two constrictions at C and E. When the rotor is displaced downward from equilibrium, the high-pressure-side constriction at C widens, and the low pressure constriction at F narrows, increasing the average pressure under the rotor and creating an upward restoring force. The opposite effect occurs for an upward perturbation. In practice, the lower surface of the rotor also acts as a shear driven pump which decreases the washout flow and alters the overall pressures involved, so the actual restoring mechanism is somewhat more complex. However, this hydrostatic balance mechanism of this further embodiment is capable of substantial restoring force to positively stabilize axial movement of the rotor.

Thus, the invention includes constructions and methods of suspending pump rotors using only passive control mechanisms, namely permanent magnetic bearings and hydrostatic pressure balancing, so that neither position sensors nor electronic feedback circuits are necessary. In these embodiments, the driver is not involved in any active way in the position control. Since it is only necessary to drive the pump rotationally at a desired pumping speed, there is no need to provide phase-varying coils of the type illustrated in FIGS. 4A–4C. It is therefore possible to operate this pump using a conventional rotating magnet driver rather than electromagnetic windings, as long as the driver-rotor thrust forces are within the limits of stability of the permanent magnet and hydrostatic forces in the pump.

Such an embodiment has several advantages. Heat generated by windings is no longer an issue. Furthermore, a hand-cranked backup mechanism may be provided in the driver. This can be implemented cheaply and dependably, with a simple belt or geared step-up coupling to the driver magnet disk, so that the blood pump driver may be hand-cranked in the event of a power failure, and the pump rotor will still be fully suspended without any mechanical contact or bearing between the rotor and the housing. Furthermore, so configured, the passively-suspended pump is readily sized to fit on currently available drivers.

In addition, the rotor may be designed with iron plates instead of the distributed permanent magnets having alternating poles of the type shown in FIG. 1A, which were necessary for driving with electromagnetic coils. In that case, the magnetic drive will exert an attractive axial force on the iron plates, providing an axial force component which may serve as a counter-bias to the axial instability of the magnetic suspension elements employed to stabilize the other degrees of motion.

The invention being thus disclosed, further variations and modifications will occur to those skilled in the art, including constructions with fewer or more magnets, constructions wherein one degree of freedom or all but one degree of freedom is passively stabilized by permanent magnets, constructions wherein all degrees of freedom are controlled by a combination of one or more passively stabilized suspension arrangements, and constructions wherein different control signals are applied to a set of windings in a flat face of a separate drive unit to drive a blood pump or actively control its suspension. All such variations are considered to lie within the scope of the invention as set forth and defined by the claims appended hereto.

What is claimed is:

1. A blood pump comprising
   a pump with a rotor, the rotor including a fluid-engaging surface for pumping blood as the rotor rotates,
   a housing for enclosing the rotor, said housing having an inlet and an outlet, for entry of blood to a compartment in said housing occupied by said rotor, and for ejection of blood by said rotor, respectively,
   a suspension system suspending the rotor in non-contact gap-defining relation with said housing without direct mechanical support between the said rotor and said housing, the suspension system including a permanent magnet spindle mounted on the rotor coaxial with a corresponding cylindrical permanent magnet carried by the housing such that the rotor rotates about a rotation axis without contact between the spindle and the cylindrical magnet, the rotor further including a plurality of permanent magnets having poles disposed circumferentially about said rotor,
   said permanent magnet spindle and said corresponding cylindrical magnet carried by the housing passively maintaining radial centering between the rotor and housing under varying applied loads,
   said rotor being shaped with a counter-flow path defined between inlet and outlet regions of said housing to define a pressure distribution on opposed surfaces of the rotor that changes as the rotor is displaced and provides a hydrostatic stabilizing force on surfaces of the rotor, and
   a driver having a plurality of drive coils aligned for imparting rotational torque to said plurality of permanent magnets to rotate said rotor at a desired speed.

2. A blood pump according to claim 1, wherein axial displacement of the rotor in the housing alters flow and changes the pressure distribution to passively and hydraulically induce an axial movement of the rotor counteracting the displacement.

3. A blood pump according to claim 1, wherein tilt of the rotor as it rotates about the rotation axis alters said pressure distribution to produce hydrostatic tilt compensation.

4. A blood pump according to claim 3, wherein said magnets and opposed surfaces of the rotor suspension system passively stabilize the rotor in radial, axial and two tilt degrees of movement, and said driver electromagnetically rotates the rotor by engaging the plurality of permanent magnets having poles disposed circumferentially about the rotor.

5. A blood pump according to claim 3, further comprising means for electromagnetically correcting tilt of said rotor.

6. A blood pump according to claim 1, wherein said housing includes two separate portions, a first portion defining a closed chamber containing said rotor, and a second portion containing said drive coils.

7. A blood pump according to claim 6, wherein said second portion engages said first portion along a flat face parallel to a face of said rotor.

8. A blood pump according to claim 6, wherein said first portion is disposable.

9. A blood pump according to claim 8, wherein said rotor includes a multi-poled disc and said housing includes a plurality of electromagnetic windings extending in a plane parallel to said disc.

10. A blood pump according to claim 1, wherein said permanent magnet spindle and said corresponding magnet carried by the housing do not introduce an axial force component therebetween.

11. A blood pump according to claim 1, wherein said permanent magnet spindle and said corresponding magnet carried by the housing introduce an axial force component therebetween.

12. A blood pump according to claim 1, wherein said driver includes a hand-cranked mechanism for rotating a magnetic disk assembly to drive the rotor in the absence of electrical power.

13. A hydrostatically stabilized blood pump comprising
    a housing having an inlet and an outlet;
    a rotor suspended within said housing, said rotor constructed and arranged to pump blood from said inlet to said outlet as said rotor rotates within said housing, said rotor being suspended within said housing by a permanent magnet assembly cooperating between said rotor and said housing; and,
    a self-adjusting flow path defined between said rotor and said housing, said self-adjusting flow path configured to provide a hydrostatic pressure distribution that introduces forces which counteract rotor displacements.

14. A blood pump according to claim 13 wherein forces from said hydrostatic pressure distribution counteracts axial displacement of said rotor.

15. A blood pump according to claim 13 wherein said self-adjusting flow path includes a restriction formed therein, said restiction generating a change in said hydrostatic pressure distribution in response to axial displacement of said rotor during operation of said pump.

16. A blood pump according to claim 15 wherein said rotor includes a central bore, wherein said restriction is provided by a stepped portion formed in said central bore.

17. A blood pump according to claim 15 wherein said restriction is provided by a spacer formed between said rotor and said housing.

18. A blood pump according to calim 13 wherein said self-adjusting flow path is continuously provided with blood flow to reduce occurrence of thrombic accumulations.

19. A blood pump according to claim 13 wherein a pressure differential between said outlet and said inlet creates a counter-flow in said self-adjusting flow path.

20. A blood pump according to claim 13 wherein tilt of said rotor as said rotor rotates during operation of said pump alters said hydrostatic pressure distribution, thereby producing forces which counteract said tilt.

21. A blood pump according to claim 13 wherein said rotor comprises:

a body; and, a plurality of axially extending vanes, said vanes and said body having a height that substantially occupies a cross-sectional height of said housing such that a resulting gap is provided between said rotor and said housing, said gap defining said self-adjusting flow path.

22. A blood pump according to claim 21 wherein said self-adjusting flow path includes an upper return path and a lower return path, with both said paths extending between a high pressure region of said pump and a low pressure region of said pump.

23. A blood pump according to claim 13 wherein said housing defines at least a closed chamber portion containing said rotor, said closed chamber portion being disposable.

24. A blood pump according to claim 13 in combination with an artificial heart.

25. A blood pump according to claim 13 in combination with a ventricular assist device.

26. A bearingless blood pump comprising:

a housing having an inlet and an outlet;

a pump rotor suspended within said housing, said rotor constructed and arranged for pumping blood from said inlet to said outlet as said rotor rotates within said housing; and, a passive suspension system to maintain a non-contact suspension of said rotor within said housing, said passive suspension system consisting of:

at least one permanent magnet assembly including a set of mutually repelling permanent magnets fixed to said rotor and said housing, respectively, and, a counter-flow path defined between said rotor and said housing, said counter-flow path configured to provide a hydrostatic pressure distribution on said rotor that introduces forces which counteract rotor displacements.

27. A blood pump according to claim 26 wherein forces from said hydrostatic pressure distribution counteracts axial displacement of said rotor.

28. A blood pump according to claim 26 wherein said counter-flow path includes a restriction formed therein, said restriction generating a change in said hydrostatic pressure distribution as said rotor axially displaces during operation of said pump.

29. A blood pump according to claim 28 wherein said rotor includes a central bore, wherein said restriction is provided by a stepped portion formed in said central bore.

30. A blood pump according to claim 28 wherein said restriction is provided by a spacer formed between said rotor and said housing.

31. A blood pump according to claim 26 wherein said counter-flow path is continuously provided with blood flow to reduce occurrence of thrombic accumulations.

32. A blood pump according to claim 26 wherein a pressure differential between said outlets and said inlet creates a counter-flow of blood in said counter-flow path.

33. A blood pump according to claim 26 wherein tilt of said rotor as said rotor rotates during operation of said pump alters said hydrostatic pressure distribution, thereby producing forces which counteract said tilt.

34. A blood pump according to claim 26 wherein said rotor comprises:

a body; and, a plurality of axially extending vanes, said vanes and said body having a height that substantially occupies a cross-sectional height of said housing such that a resulting gap is provided between said rotor and said housing, said gap defining said counter-flow path.

35. A blood pump according to claim 34 wherein said counter-flow path includes an upper return path and a lower return path, with bore said paths extending between a high pressure region of said pump and a low pressure region of said pump.

36. A blood pump according to claim 26 wherein said housing defines at least a closed chamber portion containing said rotor, said closed chamber portion being disposable.

37. A blood pump according to claim 26 in combination with an artificial heart.

38. A blood pump according to claim 26 in combination with a ventricular assist device.

39. A blood pump according to claim 26 wherein said permanent magnet assembly includes a pair of concentrically nested permanent magnets.

40. A blood pump according to claim 26 wherein said magnet assembly comprises a magnet disposed on said rotor, said rotor, together with said magnet, having a density approximating an average density of blood.

41. A blood pump according to claim 26 wherein said permanent magnet assembly comprises two axially spaced sets of magnets.

42. A blood pump according to claim 26 wherein said permanent magnet assembly comprises two pairs of concentric cylindrical magnets, said pairs lying in a common plane.

43. A blood pump according to claim 42 wherein said two pairs of concentric cylindrical magnets comprises a first central pair of magnets having parallel axial magnetization and a second outer pair of magnets having antiparallel magnetization.

44. A blood pump according to claim 43 wherein said first central pair of magnets includes a permanent magnet spindle mounted on said rotor coaxial with a corresponding cylindrical magnet carried by the housing and wherein said second outer pair of magnets includes a cylindrical magnet mounted on said rotor at a periphery thereof which rotates within a surrounding cylindrical magnet mounted in the housing.

45. A blood pump according to claim 26 wherein said permanent magnet assembly introduces an axial force.

46. A blood pump according to claim 26 wherein said permanent magnet assembly does not introduce an axial force.

47. A blood pump according to claim 26 wherein said permanent magnet assembly comprises a magnet disposed around a periphery of said rotor cooperating with a corresponding magnet disposed outside said housing, said magnets producing a repulsive force therebetween which reduces excessive tilt of said rotor.

48. A blood pump comprising:

a housing; and a rotor freely suspended within said housing, said rotor constructed and arranged for pumping blood from said inlet to said outlet as said rotor rotates within said housing, said rotor being radially and angularly suspended by at least one permanent magnet bearing assembly while axial instability of said rotor is compensated by hydrostatic balancing of pressure of blood surrounding said rotor.

49. A blood pump according to claim 48 wherein said rotor comprises:

a body; and, a plurality of axially extending vanes, said vanes and said body having a height that substantially occupies a cross-sectional height of said housing such that a resulting gap is provided between said rotor and said housing, said gap defining a counter-flow path.

50. A blood pump according to claim 49 wherein said counter-flow path includes a restriction formed therein, said restriction generating a change in said hydrostatic pressure distribution as said rotor axially displaces during operation of said pump.

51. A blood pump according to claim 50 wherein said rotor includes a central bore, wherein said restriction is provided by a stepped portion formed in said central bore.

52. A blood pump according to claim 50 wherein said restriction is provided by a spacer formed between said rotor and said housing.

53. A blood pump according to claim 49 wherein said counter-flow path is continuously provided with blood flow to reduce occurrence of thrombic accumulations.

54. A blood pump according to claim 49 wherein a pressure differential between said outlet and said inlet creates a counter-flow in said counter-flow path.

55. A blood pump according to claim 49 wherein said counter-flow path includes an upper return path and a lower return path, with both said paths extending between a high pressure region of said pump and a low pressure region of said pump.

56. A blood according to claim 48 wherein said housing defines at least a closed chamber portion containing said rotor, said closed chamber portion being disposable.

57. A blood pump according to claim 48 in combination with an artificial heart.

58. A blood pump according to claim 48 in combination with a ventricular assist device.

59. A blood pump according to claim 48 wherein said permanent magnet bearing assembly comprises two axially spaced sets of magnets.

60. A blood pump according to claim 48 wherein said permanent magnet bearing assembly comprises two pairs of concentric cylindrical magnets, said pairs lying in a common plane.

61. A blood pump according to claim 60 wherein said two pairs of concentric cylindrical magnets comprises a first central pair of magnets having parallel axial magnetization and a second outer pair of magnets having antiparallel magnetization.

62. A blood pump according to claim 61 wherein said first central pair of magnets includes a permanent magnet spindle mounted on said rotor coaxial with a corresponding cylindrical magnet carried by the housing and wherein said second outer pair of magnets includes a cylindrical magnet mounted on said rotor at a periphery thereof which rotates within a surrounding cylindrical magnet mounted in the housing.

63. A blood pump according to claim 48 wherein said permanent magnet bearing assembly introduces an axial force.

64. A blood according to claim 48 wherein said permanent magnet bearing assembly does not introduce an axial force.

65. A blood pump according to claim 48 wherein said permanent magnet bearing assembly comprises a magnet disposed around a periphery of said rotor cooperating with a corresponding magnet disposed outside said housing, said magnets producing a repulsive force therebetween which reduces excessive tilt of said rotor.

66. A blood pump comprising:
a housing; and,
a freely supported rotor housed within said housing such that said rotor is subject to a plurality of degrees of freedom, said rotor being actively controlled in a first degree of freedom and passively controlled in the remaining degrees of freedom, with said remaining degrees of freedom being controlled by a permanent magnet assembly and by hydrostatic balancing of pressure of blood surrounding said rotor.

67. A blood pump according to claim 66 wherein said active control of said rotor in said first degree of freedom comprises a driver for magnetically driving said rotor.

68. A blood pump according to claim 66 wherein said rotor comprises:
a body; and,
a plurality of axially extending vanes, said vanes and said body having a height that substantially occupies a cross-sectional height of said housing such that a resulting gap is provided between said rotor and said housing, said gap defining a counter-flow path.

69. A blood pump according to claim 68 wherein said counter-flow path includes a restriction formed therein, said restriction generating a change in said hydrostatic pressure distribution as said rotor axially displaces during operation of said pump.

70. A blood pump according to claim 69 wherein said rotor includes a central bore, wherein said restriction is provided by a stepped portion formed in said central bore.

71. A blood pump according to claim 69 wherein said restriction is provided by a spacer formed between said rotor and said housing.

72. A blood pump according to claim 68 wherein said counter-flow path is continuously provided with blood flow to reduce occurrence of thrombic accumulations.

73. A blood pump according to claim 68 wherein a pressure differential between said outlet and said inlet creates a counter-flow in said counter-flow path.

74. A blood pump according to claim 68 wherein said counter-flow path includes an upper return path and a lower return path, with both said paths extending between a high pressure region of said pump and a low pressure region of said pump.

75. A blood pump according to claim 66 wherein said housing defines at least a closed chamber portion containing said rotor, said closed chamber portion being disposable.

76. A blood pump according to claim 66 in combination with an artificial heart.

77. A blood pump according to claim 66 in combination with a ventricular assist device.

78. A blood pump according to claim 66 wherein said hydrostatic pressure controls an axial degree of freedom.

79. A blood pump according to claim 78 wherein said permanent magnet assembly controls radial and angular degrees of freedom.

80. A blood pump according to claim 66 wherein said permanent magnet assembly controls radial and angular degrees of freedom.

81. A method of suspending a rotor within a housing of a blood pump, said method comprising the steps of:
magnetically suspending the rotor within the housing; and,
creating a hydrostatic pressure distribution of blood surrounding the rotor such that forces caused by said hydrostatic pressure distribution acting on said rotor counteract forces tending to axial displace said rotor.

82. A method according to claim 81 further comprising the step of creating a counter-flow of continuously flowing blood around said rotor to reduce occurrence of thrombic accumulations.

83. A method according to claim 81 further comprising the step of creating a hydrostatic pressure distribution of blood surrounding the rotor such that forces caused by said hydrostatic pressure distribution acting on said rotor counteract forces tending to tilt said rotor.

84. A method according to claim 81 wherein said step of magnetically suspending the rotor within the housing comprises the step of radially suspending the rotor within the housing.

85. A method according to claim 81 wherein said step of magnetically suspending the rotor within the housing comprises the step of angularly suspending the rotor within the housing.

86. A blood pump comprising:

a housing having an inlet and an outlet;

a rotor suspended within said housing, said rotor constructed and arranged for pumping blood from said inlet to said outlet as said rotor rotates within said housing;

a magnetic suspension force generated by a permanent magnet assembly cooperating with said rotor and said housing for suspending said rotor in a predetermined position; and, a hydrostatic compensating force for counteracting axial instability of said rotor.

87. A blood pump according to claim 86 wherein said hydrostatic compensating force is generated within a counter-flow path defined between said rotor and said housing.

88. A blood pump according to claim 87 wherein said counter-flow path includes a restriction formed therein, said restriction generating a change in said hydrostatic compensating force as said rotor axially displaces during operation of said pump.

89. A blood pump according to claim 88 wherein said rotor includes a central bore, wherein said restriction is provided by a stepped portion formed in said central bore.

90. A blood pump according to claim 88 wherein said restriction is provided by a spacer formed between said rotor and said housing.

91. A blood pump according to claim 86 wherein said predetermined position comprises radial and angular positions.

92. A blood pump according to claim 86 wherein said magnetic suspension force comprises a radial force for maintaining said rotor in a predetermined radial position.

93. A blood pump according to claim 86 wherein said magnetic suspension force comprises an axial force acting on a periphery of said rotor for maintaining said rotor in a predetermined angular position.

94. A blood pump comprising:

a housing having a cylindrical permanent magnet defining a rotation axis; and, a rotor having a permanent magnet spindle coaxial with said rotation axis, said magnets passively maintaining radial centering between said rotor and said housing, with said rotor being shaped with a counter-flow path to define a hydrostatic pressure distribution on opposed surfaces of said rotor that changes as said rotor is displaced and provides a hydrostatic stabilizing force on surfaces of said rotor.

95. A blood pump according to claim 94, wherein axial displacement of the rotor in the housing alters flow and changes said hydrostatic pressure distribution to passively and hydraulically induce an axial movement of the rotor counteracting the displacement.

96. A blood pump according to claim 94, wherein tilt of the rotor as said rotor rotates about the rotation axis alters said hydrostatic pressure distribution to produce hydrostatic tilt compensation.

97. A blood pump according to claim 96 wherein said magnets and opposed surfaces of the rotor suspension system passively stabilize the rotor in radial, axial and two tilt degrees of movement.

* * * * *

UNITED STATES PATENT AND TRADEMARK OFFICE
CERTIFICATE OF CORRECTION

PATENT : 6,071,093
DATED : June 6, 2000
INVENTOR(S) : Robert M. Hart

Page 1 of 2

It is certified that error appears in the above-identified patent and that said Letters Patent is hereby corrected as shown below:

On the cover page, under [73] delete "Danvers, Inc." and add --Danvers, Mass.--;
Column 2, Line 12 before "generator" delete "(";
Column 3, Line 12 after "magnets" delete "are" and add --is--;
Column 3, Line 47 delete "detect and add --detects--;
Column 3, Line 48 delete "develop" and add --develops--;
Column 5, Line 2 delete "are" and add --is--;
Column 5, Line 52 delete "arc" and add --are--;
Column 5, Line 60 delete "(20C FIG. 1A)" and add -- 20(FIG. 1A);
Column 10, Line 7 delete "mutation" and add -- nutation--;
Column 10, Line 41 delete "verical " and add -- vertical--;

UNITED STATES PATENT AND TRADEMARK OFFICE
CERTIFICATE OF CORRECTION

PATENT NO.  : 6,071,093
DATED       : June 6, 2000
INVENTOR(S) : Robert M. Hart

It is certified that error appears in the above-identified patent and that said Letters Patent is hereby corrected as shown below:

Column 13, Line 6 delete "Er" and add --Kr.--;
Column 14, Line 33 delete "F" and add --E--;
Column 16, Line 43 delete "counteracts" and add --counteract--;
Column 16, Line 56 delete "calim" and add --claim--;
Column 17, Line 37 delete "counteracts" and add --counteract--;
Column 17 Line 54 delete "outlets" and add --outlet--;
Column 18, Line 27 delete "comprises" and add --comprise--;
Column 19, Line 23 delete "clood according" and add --blood pump according--;
Column 19, Line 38 delete "comprises" and add --comprise--; and
Column 20, Line 58 delete "axial displace" and add --axially displace--.

Signed and Sealed this

Twenty-fourth Day of April, 2001

Attest:

NICHOLAS P. GODICI

Attesting Officer        Acting Director of the United States Patent and Trademark Office